United States Patent
Saoji et al.

(10) Patent No.: US 8,467,881 B2
(45) Date of Patent: Jun. 18, 2013

(54) METHODS AND SYSTEMS FOR REPRESENTING DIFFERENT SPECTRAL COMPONENTS OF AN AUDIO SIGNAL PRESENTED TO A COCHLEAR IMPLANT PATIENT

(75) Inventors: Aniket Saoji, Northridge, CA (US); Leonid M. Litvak, Los Angeles, CA (US)

(73) Assignee: Advanced Bionics, LLC, Valencia, CA (US)

( * ) Notice: Subject to any disclaimer, the term of this patent is extended or adjusted under 35 U.S.C. 154(b) by 920 days.

(21) Appl. No.: 12/569,500

(22) Filed: Sep. 29, 2009

(65) Prior Publication Data
US 2011/0077710 A1    Mar. 31, 2011

(51) Int. Cl.
*A61N 1/36* (2006.01)
(52) U.S. Cl.
USPC .................... 607/57; 607/55; 607/56
(58) Field of Classification Search
USPC ............ 607/55, 56, 57, 62, 137; 623/10
See application file for complete search history.

(56) References Cited

U.S. PATENT DOCUMENTS

| | | | |
|---|---|---|---|
| 5,095,904 A * | 3/1992 | Seligman et al. | 607/57 |
| 5,550,924 A * | 8/1996 | Helf et al. | 381/94.3 |
| 2003/0167077 A1* | 9/2003 | Blamey et al. | 607/57 |
| 2005/0177205 A1 | 8/2005 | Kwon et al. | |
| 2006/0149337 A1* | 7/2006 | John | 607/45 |
| 2006/0247735 A1* | 11/2006 | Honert | 607/57 |
| 2006/0265061 A1* | 11/2006 | Kwon et al. | 623/10 |

* cited by examiner

*Primary Examiner* — Christopher D Koharski
*Assistant Examiner* — Pamela M Bays
(74) *Attorney, Agent, or Firm* — ALG Intellectual Property, LLC

(57) ABSTRACT

An exemplary method of representing different spectral components of an audio signal presented to a cochlear implant patient includes identifying one or more spectral peaks of an audio signal presented to a cochlear implant patient, applying electrical stimulation representative of the one or more spectral peaks to at least one stimulation site within the cochlear implant patient using a partial multipolar stimulation configuration, and applying electrical stimulation representative of one or more other spectral components of the audio signal to at least one other stimulation site within the cochlear implant patient using a monopolar stimulation configuration. Corresponding methods and systems are also disclosed.

9 Claims, 11 Drawing Sheets

METHODS AND SYSTEMS FOR REPRESENTING DIFFERENT SPECTRAL COMPONENTS OF AN AUDIO SIGNAL PRESENTED TO A COCHLEAR IMPLANT PATIENT

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous cochlear implant systems—or cochlear prostheses—have been developed. Cochlear implant systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea. The electrodes form a number of stimulation channels through which electrical stimulation pulses may be applied directly to auditory nerves within the cochlea. An audio signal may then be presented to a patient by translating the audio signal into a number of electrical stimulation pulses and applying the stimulation pulses directly to the auditory nerve within the cochlea via one or more of the electrodes.

Some audio signals, such as speech, contain spectral peaks that represent the distinguishing or meaningful frequency components of the audio signals. It is therefore desirable to present electrical stimulation representative of such spectral peaks to a cochlear implant patient in as fine of spectral resolution as possible. However, traditional monopolar stimulation configurations that are often used to apply electrical stimulation to the auditory nerve produce a broad spread of electrical excitation and therefore result in relatively poor spectral resolution.

SUMMARY

An exemplary method of representing different spectral components of an audio signal presented to a cochlear implant patient includes identifying one or more spectral peaks of an audio signal presented to a cochlear implant patient, applying electrical stimulation representative of the one or more spectral peaks to at least one stimulation site within the cochlear implant patient using a partial multipolar stimulation configuration, and applying electrical stimulation representative of one or more other spectral components of the audio signal to at least one other stimulation site within the cochlear implant patient using a monopolar stimulation configuration.

An exemplary system for representing different spectral components of an audio signal presented to a cochlear implant patient includes a sound processor configured to identify one or more spectral peaks of an audio signal presented to a cochlear implant patient and an implantable cochlear stimulator communicatively coupled to the sound processor and configured to apply electrical stimulation representative of the one or more spectral peaks to at least one stimulation site within the cochlear implant patient using a partial multipolar stimulation configuration and apply electrical stimulation representative of one or more other spectral components of the audio signal to at least one other stimulation site within the cochlear implant patient using a monopolar stimulation configuration.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
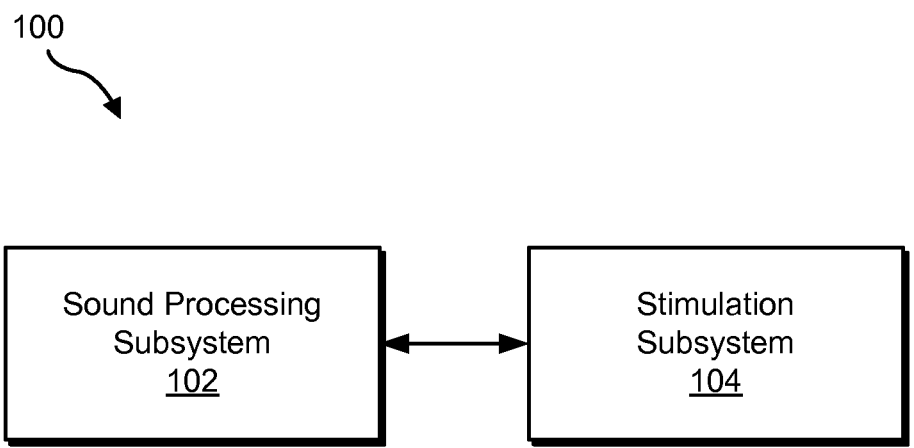
FIG. 1 illustrates an exemplary cochlear implant system according to principles described herein.

Methods and systems for representing different spectral components of an audio signal presented to a cochlear implant patient are described herein. In some examples, one or more spectral peaks of an audio signal presented to a cochlear implant patient are identified. Electrical stimulation representative of the one or more spectral peaks is applied to at least one stimulation site within the cochlear implant patient using a partial multipolar stimulation configuration. Electrical stimulation representative of one or more other spectral components of the audio signal to at least one other stimulation site within the cochlear implant patient using a monopolar stimulation configuration.

As used herein, a "spectral peak" refers to a spectral component within an audio signal that represents a distinguishing or meaningful component of the audio signal. A spectral peak may have an amplitude that is relatively greater than surrounding frequency components.

As used herein, a "monopolar stimulation configuration" is one in which stimulation current is passed through a single intracochlear electrode (i.e., an electrode that is implanted within the cochlea) and an extracochlear ground electrode (i.e., an electrode located outside the cochlea). Hence, in monopolar stimulation, all of the current flows between the intracochlear electrode and the extracochlear ground electrode. The extracochlear ground electrode may be implemented using the case of the implantable cochlear stimulator, disposed on a proximal portion of a lead that is inserted into the cochlea, and/or otherwise implemented in any suitable manner. In some alternatively embodiments, an intracochlear electrode may be used as the ground electrode.

As used herein, a "full multipolar stimulation configuration" is one in which stimulation current is simultaneously applied to a main intracochlear electrode and one or more intracochlear compensating electrodes without any of the stimulation current flowing to the extracochlear electrode. Hence, all of the current flows between the main intracochlear electrode and the one or more intracochlear compensating electrodes. Exemplary full multipolar stimulation configurations include, but are not limited to, full bipolar stimulation (where stimulation current is passed between two intracochlear electrodes) and full tripolar stimulation (where stimulation current is passed between three intracochlear electrodes).

As used herein, a "partial multipolar stimulation configuration" is one in which stimulation current is applied to a main intracochlear electrode while compensating current opposite in phase to that of the stimulation current is simultaneously applied to one or more intracochlear compensating electrodes. In partial multipolar stimulation, the total amount of compensating current applied to the compensating electrodes is less than the total amount of stimulation current applied to the main electrode. The remaining amount of current flows to the extracochlear ground electrode. For example, as will be described in more detail below, the amount of stimulation current applied to the main electrode may be represented by $I_0$ and the amount of stimulation current applied to the compensating electrodes may be represented by $\sigma*I_0$, where $\sigma$ is greater than zero and less than one. Hence, the remaining amount of current that flows to the extracochlear ground electrode may be represented by $(1-\sigma)*I_0$.

By selectively representing spectral peaks with a partial multipolar stimulation configuration and other spectral components with a monopolar stimulation configuration, enhanced spectral resolution, more accurate conveyance of information contained within an audio signal, and/or optimal speech recognition may be achieved. Moreover, spectral smearing may be minimized, thereby improving performance of a cochlear implant system.

FIG. 1 illustrates an exemplary cochlear implant system 100. As shown in FIG. 1, cochlear implant system 100 may include a sound processing subsystem 102 and a stimulation subsystem 104 configured to communicate with one another. As will be described in more detail below, cochlear implant system 100 may be configured to selectively utilize a partial multipolar electrode configuration to apply electrical stimulation representative of one or more spectral peaks of an audio signal to a cochlear implant patient and a monopolar electrode stimulation to apply electrical stimulation representative of one or more other spectral components of the audio signal to the cochlear implant patient.

In some examples, sound processing subsystem 102 may be configured to detect or sense an audio signal and divide the audio signal into a plurality of analysis channels each containing a frequency domain signal (or simply "signal") representative of a distinct frequency portion of the audio signal. Sound processing subsystem 102 may be further configured to identify one or more spectral peaks included within the frequency domain signals and direct stimulation subsystem 104 to use a partial multipolar stimulation configuration to generate and apply electrical stimulation representative of the one or more spectral peaks to a cochlear implant patient. Sound processing subsystem 102 may additionally be configured to detect one or more spectral valleys and/or other spectral components of the audio signal and direct stimulation subsystem 104 to use a monopolar stimulation configuration to generate and apply electrical stimulation representative of the one or more other spectral components spectral peaks to the cochlear implant patient.

Stimulation subsystem 104 may be configured to generate and apply electrical stimulation (also referred to herein as "stimulation current" and/or "stimulation pulses") to one or more stimulation sites within the cochlea of a patient as directed by sound processing subsystem 102. For example, stimulation subsystem 104 may be configured to generate and apply electrical stimulation in accordance with one or more stimulation parameters transmitted thereto by sound processing subsystem 102. The stimulation parameters may control various parameters of the electrical stimulation applied to a stimulation site including, but not limited to, a stimulation configuration, a frequency, a pulse width, an amplitude, a waveform (e.g., square or sinusoidal), an electrode polarity (i.e., anode-cathode assignment), a location (i.e., which electrode pair or electrode group receives the stimulation current), a burst pattern (e.g., burst on time and burst off time), a duty cycle or burst repeat interval, a spectral tilt, a ramp on time, and a ramp off time of the stimulation current that is applied to the stimulation site.

Figure 2:
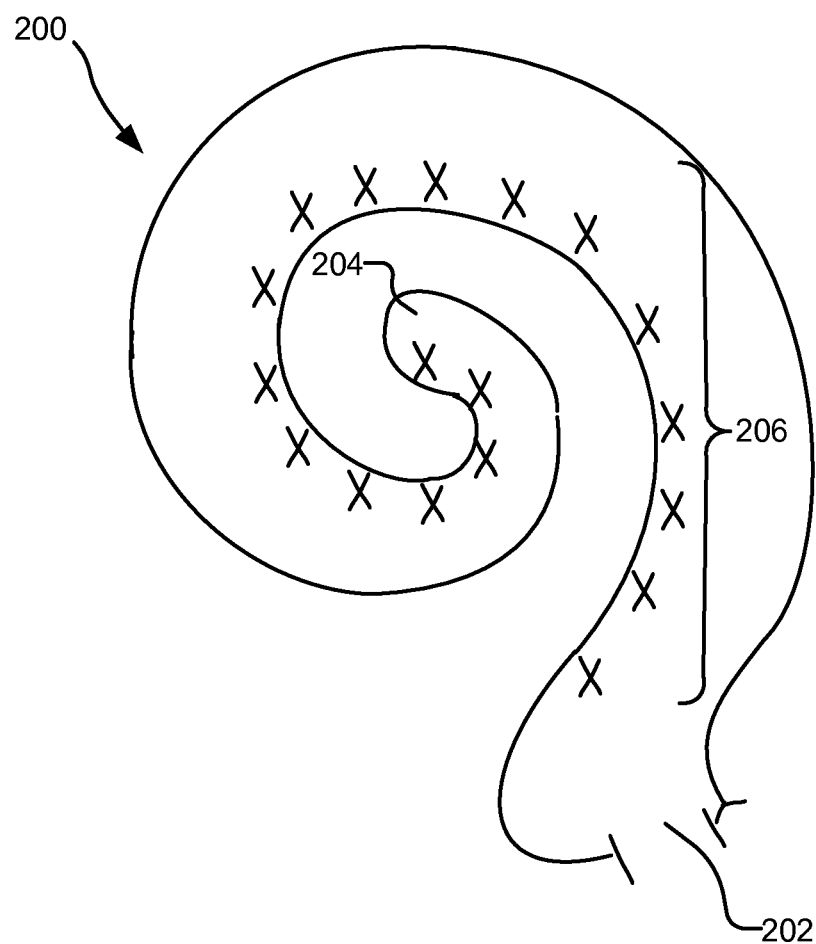
FIG. 2 illustrates a schematic structure of the human cochlea according to principles described herein.

The one or more stimulation sites to which electrical stimulation is applied may include any target area or location within the cochlea. FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 104 may therefore be configured to apply electrical stimulation to different locations within the cochlea 200 (e.g., different locations along the auditory nerve tissue 206) to provide a sensation of hearing.

Returning to FIG. 1, sound processing subsystem 102 and stimulation subsystem 104 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

Cochlear implant system 100, including sound processing subsystem 102 and stimulation subsystem 104, may include any hardware, computer-implemented instructions (e.g., software), firmware, or combinations thereof configured to perform one or more of the processes described herein. For example, cochlear implant system 100, including sound processing subsystem 102 and stimulation subsystem 104, may include hardware (e.g., one or more signal processors and/or other computing devices) configured to perform one or more of the processes described herein.

One or more of the processes described herein may be implemented at least in part as instructions executable by one or more computing devices. In general, a processor receives instructions from a computer-readable medium (e.g., a memory, etc.) and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computing device (e.g., by a processor within sound processing subsystem 102). Such a medium may take many forms, including, but not limited to, non-volatile media and/or volatile media. Exemplary computer-readable media that may be used in accordance with the systems and methods described herein include, but are not limited to, random access memory ("RAM"), dynamic RAM, a PROM, an EPROM, a FLASH-EEPROM, any other memory chip or cartridge, or any other medium from which a computing device can read.

Figure 3:
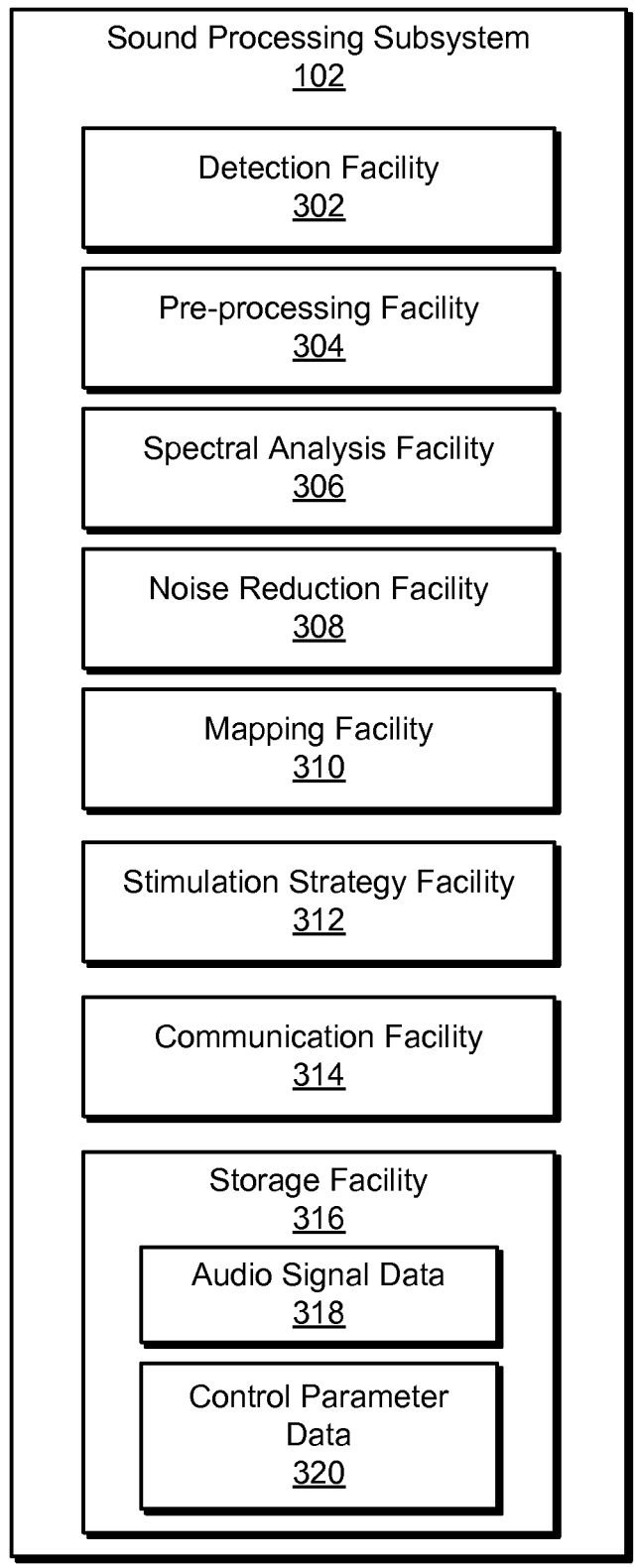
FIG. 3 illustrates exemplary components of a sound processing subsystem according to principles described herein.

FIG. 3 illustrates exemplary components of sound processing subsystem 102. As shown in FIG. 3, sound processing subsystem 102 may include a detection facility 302, a pre-processing facility 304, a spectral analysis facility 306, a noise reduction facility 308, a mapping facility 310, a stimulation strategy facility 312, a communication facility 314, and a storage facility 316, which may be in communication with one another using any suitable communication technologies. Each of these facilities 302-316 may include any combination of hardware, software, and/or firmware as may serve a particular application. For example, one or more of facilities 302-316 may include a computing device or processor configured to perform one or more of the functions described herein. Facilities 302-316 will now be described in more detail.

Detection facility 302 may be configured to detect or sense one or more audio signals and convert the detected signals to corresponding electrical signals. To this end, detection facility 302 may include a microphone or other transducer. In some examples, the one or more audio signals may include speech. The one or more audio signals may additionally or alternatively include music, ambient noise, and/or other sounds.

Pre-processing facility 304 may be configured to perform various signal processing operations on the one or more audio signals detected by detection facility 302. For example, pre-processing facility 304 may amplify a detected audio signal, convert the audio signal to a digital signal, filter the digital signal with a pre-emphasis filter, subject the digital signal to automatic gain control, and/or perform one or more other signal processing operations on the detected audio signal.

Spectral analysis facility 306 may be configured to divide the audio signal into a plurality of analysis channels each containing a frequency domain signal representative of a distinct frequency portion of the audio signal. For example, spectral analysis facility 306 may include a plurality of bandpass filters configured to divide the audio signal into a plurality of frequency channels or bands. Additionally or alternatively, spectral analysis facility 306 may be configured to convert the audio signal from a time domain into a frequency domain and then divide the resulting frequency bins into the plurality of analysis channels. To this end, spectral analysis facility 206 may include one or more components configured to apply a Discrete Fourier Transform (e.g., a Fast Fourier Transform ("FFT")) to the audio signal.

Spectral analysis facility 306 may be configured to divide the audio signal into any number of analysis channels as may serve a particular application. In some examples, the total number of analysis channels is set to be less than or equal to a total number of stimulation channels through which electrical stimulation representative of the audio signal is applied to a cochlear implant patient.

Spectral analysis facility 306 may be further configured to analyze an acoustic spectrum of the audio signal and identify one or more spectral peaks included therein. For example, spectral analysis facility 306 may be configured to identify one or more formants included in a speech or music signal and/or any other type of spectral peak as may serve a particular application. As used herein, a "formant" is a spectral component representative of a vowel sound or other distinguishing feature of an audio signal.

Spectral analysis facility 306 may be configured to identify spectral peaks in any suitable manner. In some examples, spectral analysis facility 306 may identify spectral peaks by detecting a maximum energy level of each of the frequency domain signals included in the analysis channels and then designating a predetermined number of the highest maximum energy levels (and their corresponding frequency domain signals) as corresponding to spectral peaks. For example, if there are sixteen analysis channels, spectral analysis facility 306 may designate the eight (or any other number) highest detected maximum energy levels as corresponding to spectral peaks.

Alternatively, spectral analysis facility 306 may identify spectral peaks by detecting a maximum energy level of each of the frequency domain signals included in the analysis channels and then designating all of the maximum energy levels (and their corresponding frequency domain signals) that are greater than a predetermined threshold value as corresponding to spectral peaks. For example, if only three out of sixteen detected maximum energy levels are greater than a predetermined threshold value, then only the three detected maximum energy levels are identified as corresponding to spectral peaks.

Other spectral analysis heuristics may be used by spectral analysis facility 306 to identify spectral peaks as may serve a particular application. For example, spectral analysis facility 306 may be configured to detect an average energy level contained within each analysis channel and designate the average energy levels that are greater than a predetermined threshold as corresponding to spectral peaks.

Spectral analysis facility 306 may additionally or alternatively be configured to identify one or more other spectral components (e.g., spectral valleys) of an audio signal. For example, spectral analysis facility 306 may detect a maximum energy level of each of the frequency domain signals included in the analysis channels and designate all of the maximum energy levels (and their corresponding frequency domain signals) that are less than a predetermined threshold value as corresponding to spectral valleys. Additional or alternative spectral analysis heuristics may be used to identify spectral valleys and/or other spectral components of an audio signal as may serve a particular application.

Noise reduction facility 308 may be configured to apply noise reduction to the signals within the analysis channels in accordance with any suitable noise reduction heuristic as may serve a particular application. For example, noise reduction facility 308 may be configured to generate a noise reduction gain parameter for each of the signals within the analysis channels and apply noise reduction to the signals in accordance with the determined noise reduction gain parameters. It will be recognized that in some implementations, noise reduction facility 308 is omitted from sound processing subsystem 102.

Mapping facility 310 may be configured to map the signals within the analysis channels to electrical stimulation pulses to be applied to a patient via one or more stimulation channels. For example, signal levels of the noise reduced signals within the analysis channels are mapped to amplitude values used to define electrical stimulation pulses that are applied to the patient by stimulation subsystem 104 via one or more corresponding stimulation channels. Mapping facility 310 may be further configured to perform additional processing of the noise reduced signals contained within the analysis channels, such as signal compression.

Stimulation strategy facility 312 may be configured to select a particular stimulation configuration in which stimulation subsystem 104 operates to generate and apply electrical stimulation representative of various spectral components of an audio signal. To this end, stimulation strategy facility 312 may generate one or more stimulation parameters based on the frequency domain signals within the analysis channels. For example, stimulation strategy facility 312 may be configured to generate stimulation parameters that direct stimulation subsystem 104 to use partial multipolar stimulation to generate and apply electrical stimulation representative of the one or more spectral peaks identified by spectral analysis facility 306. Stimulation strategy facility 312 may additionally be configured to generate stimulation parameters that direct stimulation subsystem 104 to use monopolar stimulation to generate and apply electrical stimulation representative of the one or more other spectral components of an audio signal as identified by spectral analysis facility 306.

Stimulation strategy facility 312 may additionally or alternatively be configured to generate stimulation parameters that direct stimulation subsystem 104 to use current steering to apply electrical stimulation to one or more stimulation sites within a cochlear implant patient. Exemplary current steering strategies that may be selected by stimulation strategy facility 312 will be described in more detail below.

Communication facility 314 may be configured to facilitate communication between sound processing subsystem 102 and stimulation subsystem 104. For example, communication facility 314 may include one or more coils configured to transmit control signals (e.g., the one or more stimulation parameters generated by stimulation strategy facility 312) and/or power via one or more communication links to stimulation subsystem 104. Additionally or alternatively, communication facility 314 may one or more wires or the like that are configured to facilitate direct communication with stimulation subsystem 104.

Storage facility 316 may be configured to maintain audio signal data 318 representative of an audio signal detected by detection facility 302 and control parameter data 320 representative of one or more control parameters, which may include one or more stimulation parameters to be transmitted from sound processing subsystem 102 to stimulation subsystem 104. Storage facility 316 may be configured to maintain additional or alternative data as may serve a particular application.

Figure 4:
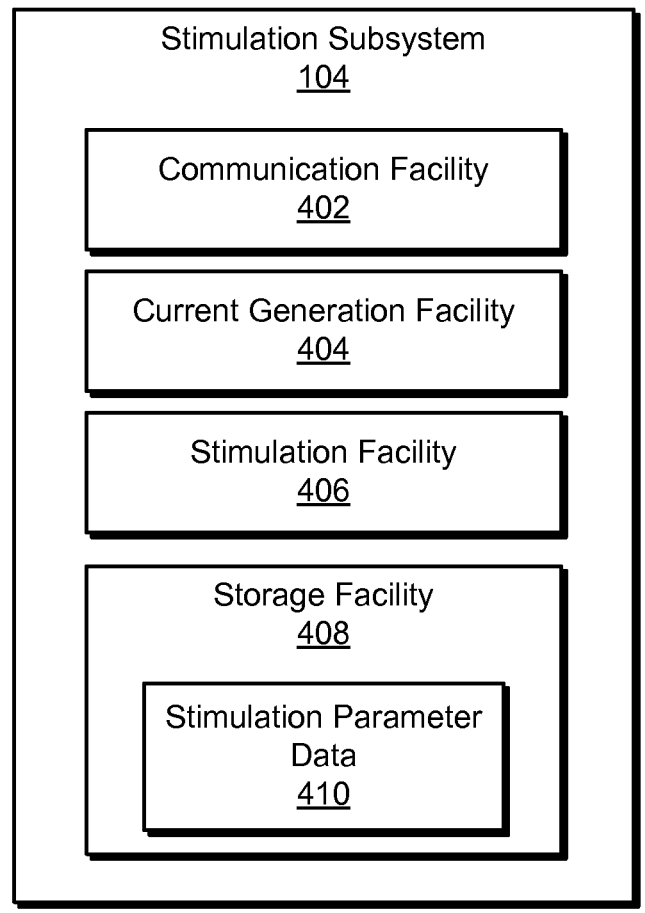
FIG. 4 illustrates exemplary components of a stimulation subsystem according to principles described herein.

FIG. 4 illustrates exemplary components of stimulation subsystem 104. As shown in FIG. 4, stimulation subsystem 104 may include a communication facility 402, a current generation facility 404, a stimulation facility 406, and a storage facility 408, which may be in communication with one another using any suitable communication technologies. Each of these facilities 402-408 may include any combination of hardware, software, and/or firmware as may serve a particular application. For example, one or more of facilities 402-408 may include a computing device or processor configured to perform one or more of the functions described herein. Facilities 402-408 will now be described in more detail.

Communication facility 402 may be configured to facilitate communication between stimulation subsystem 104 and sound processing subsystem 102. For example, communication facility 402 may include one or more coils configured to receive control signals and/or power via one or more communication links to stimulation subsystem 104. Communication facility 402 may additionally or alternatively be configured to transmit one or more status signals and/or other data to sound processing subsystem 102.

Current generation facility 404 may be configured to generate electrical stimulation in accordance with one or more stimulation parameters received from sound processing subsystem 102. To this end, current generation facility 404 may include one or more current generators and/or any other circuitry configured to facilitate generation of electrical stimulation. For example, current generation facility 404 may be configured to generate electrical stimulation representative of one or more spectral peaks and/or one or more other spectral components (e.g., spectral valleys) of an audio signal.

Stimulation facility 406 may be configured to apply the electrical stimulation generated by current generation facility 404 to one or more stimulation sites within the cochlea of a patient in accordance with the one or more stimulation parameters generated by stimulation strategy facility 312. To this end, as will be illustrated in more detail below, stimulation facility 406 may include one or more electrodes disposed on a lead that may be inserted within the cochlea. For example, stimulation facility 406 may be configured to apply electrical stimulation representative of one or more spectral peaks of an audio signal as identified by spectral analysis facility 306 to at least one stimulation site within the cochlear implant patient using a partial multipolar stimulation configuration. Stimulation facility 406 may be further configured to apply electrical stimulation representative of one or more other spectral components (e.g., spectral valleys) of the audio signal to at least one other stimulation site within the cochlear implant patient using a monopolar stimulation configuration.

Storage facility 408 may be configured to maintain stimulation parameter data 410 as received from sound processing subsystem 102. Stimulation parameter data 410 may be representative of one or more stimulation parameters configured to define the electrical stimulation generated and applied by stimulation subsystem 104. Storage facility 408 may be configured to maintain additional or alternative data as may serve a particular application.

Figure 5:
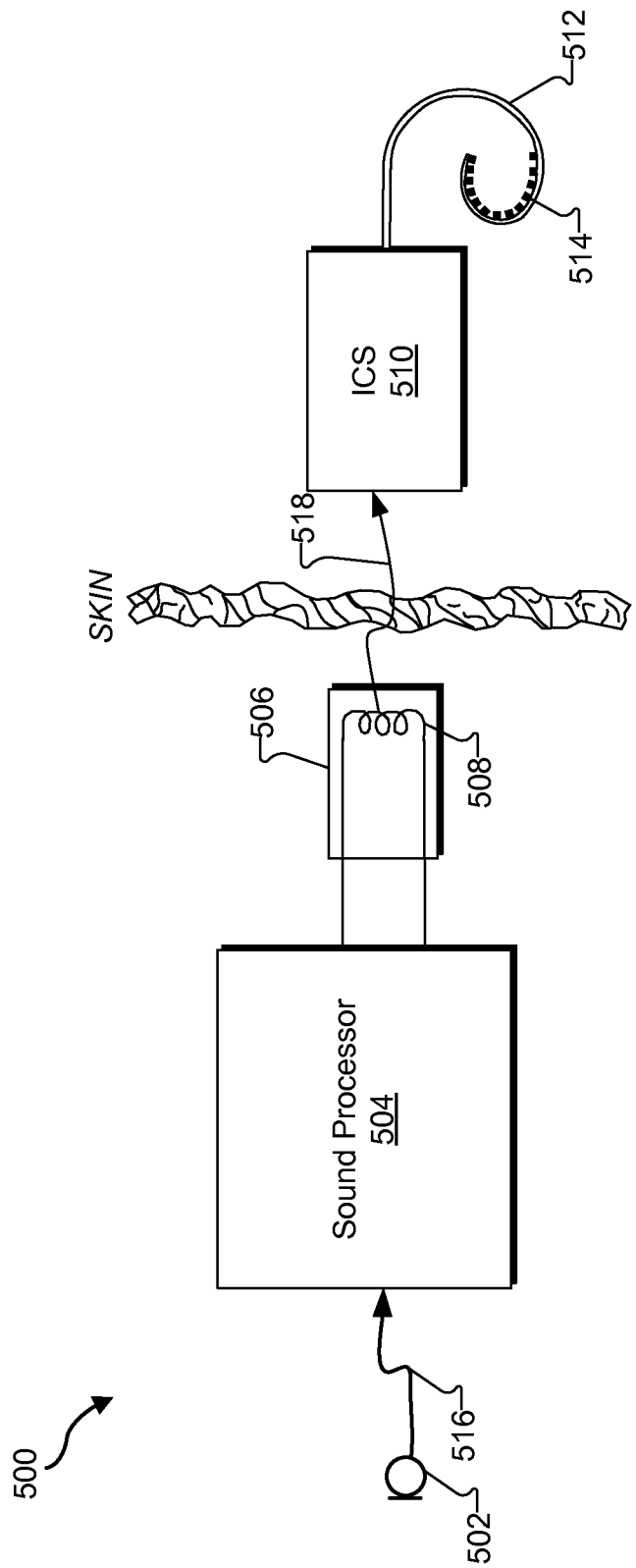
FIG. 5 illustrates an exemplary implementation of the cochlear implant system of FIG. 1 according to principles described herein.

FIG. 5 illustrates an exemplary implementation 500 of cochlear implant system 100. As shown in FIG. 5, implementation 500 may include a microphone 502, a sound processor 504, a headpiece 506 having a coil 508 disposed therein, an implantable cochlear stimulator ("ICS") 510, a lead 512, and a plurality of electrodes 514 disposed on the lead 512. Additional or alternative components may be included within implementation 500 of cochlear implant system 100 as may serve a particular application. The facilities described herein may be implemented by or within one or more components shown within FIG. 5. For example, detection facility 302 may be implemented by microphone 502. Pre-processing facility 304, spectral analysis facility 306, noise reduction facility 308, mapping facility 310, stimulation strategy facility 312, and/or storage facility 316 may be implemented by sound processor 504. Communication facility 314 may be implemented by headpiece 506 and coil 508. Communication facility 402, current generation facility 404, and storage facility 408 may be implemented by implantable cochlear stimulator 508. Stimulation facility 406 may be implemented by lead 510 and electrodes 512.

As shown in FIG. 5, microphone 502, sound processor 504, and headpiece 506 may be located external to a cochlear implant patient. In some alternative examples, microphone 502 and/or sound processor 504 may be implanted within the patient. In such configurations, the need for headpiece 506 may be obviated.

Microphone 502 may detect an audio signal and convert the detected signal to a corresponding electrical signal. Microphone 502 may be placed external to the patient, within the ear canal of the patient, or at any other suitable location as may serve a particular application. The electrical signal may be sent from microphone 502 to sound processor 504 via a communication link 514, which may include a telemetry link, a wire, and/or any other suitable communication link.

Sound processor 504 is configured to process the converted audio signal in accordance with a selected sound processing strategy to generate appropriate stimulation parameters for controlling implantable cochlear stimulator 510. Sound processor 504 may include or be implemented within a behind-the-ear ("BTE") unit, a portable speech processor ("PSP"), and/or any other sound processing unit as may serve a particular application. Exemplary components of sound processor 504 will be described in more detail below.

Sound processor 504 may be configured to transcutaneously transmit data (e.g., data representative of one or more stimulation parameters) to implantable cochlear stimulator 504 via coil 508. As shown in FIG. 5, coil 508 may be housed within headpiece 506, which may be affixed to a patient's head and positioned such that coil 508 is communicatively coupled to a corresponding coil (not shown) included within implantable cochlear stimulator 510. In this manner, data may be wirelessly transmitted between sound processor 504 and implantable cochlear stimulator 510 via communication link 518. It will be understood that data communication link 118 may include a bi-directional communication link and/or one or more dedicated uni-directional communication links. In some alternative embodiments, sound processor 504 and implantable cochlear stimulator 510 may be directly connected with one or more wires or the like.

Implantable cochlear stimulator 510 may be configured to generate electrical stimulation representative of an audio signal detected by microphone 502 in accordance with one or more stimulation parameters transmitted thereto by sound processing subsystem 102. Implantable cochlear stimulator 510 may be further configured to apply the electrical stimulation to one or stimulation sites within the cochlea via one or more electrodes 514 disposed along lead 512. Hence, implantable cochlear stimulator 510 may be referred to as a multi-channel implantable cochlear stimulator 510.

To facilitate application of the electrical stimulation generated by implantable cochlear stimulator 510, lead 512 may be inserted within a duct of the cochlea such that electrodes 514 are in communication with one or more stimulation sites within the cochlea. As used herein, the term "in communication with" refers to electrodes 514 being adjacent to, in the general vicinity of, in close proximity to, directly next to, or directly on the stimulation site. Any number of electrodes 514 (e.g., sixteen) may be disposed on lead 512 as may serve a particular application.

Figure 6:
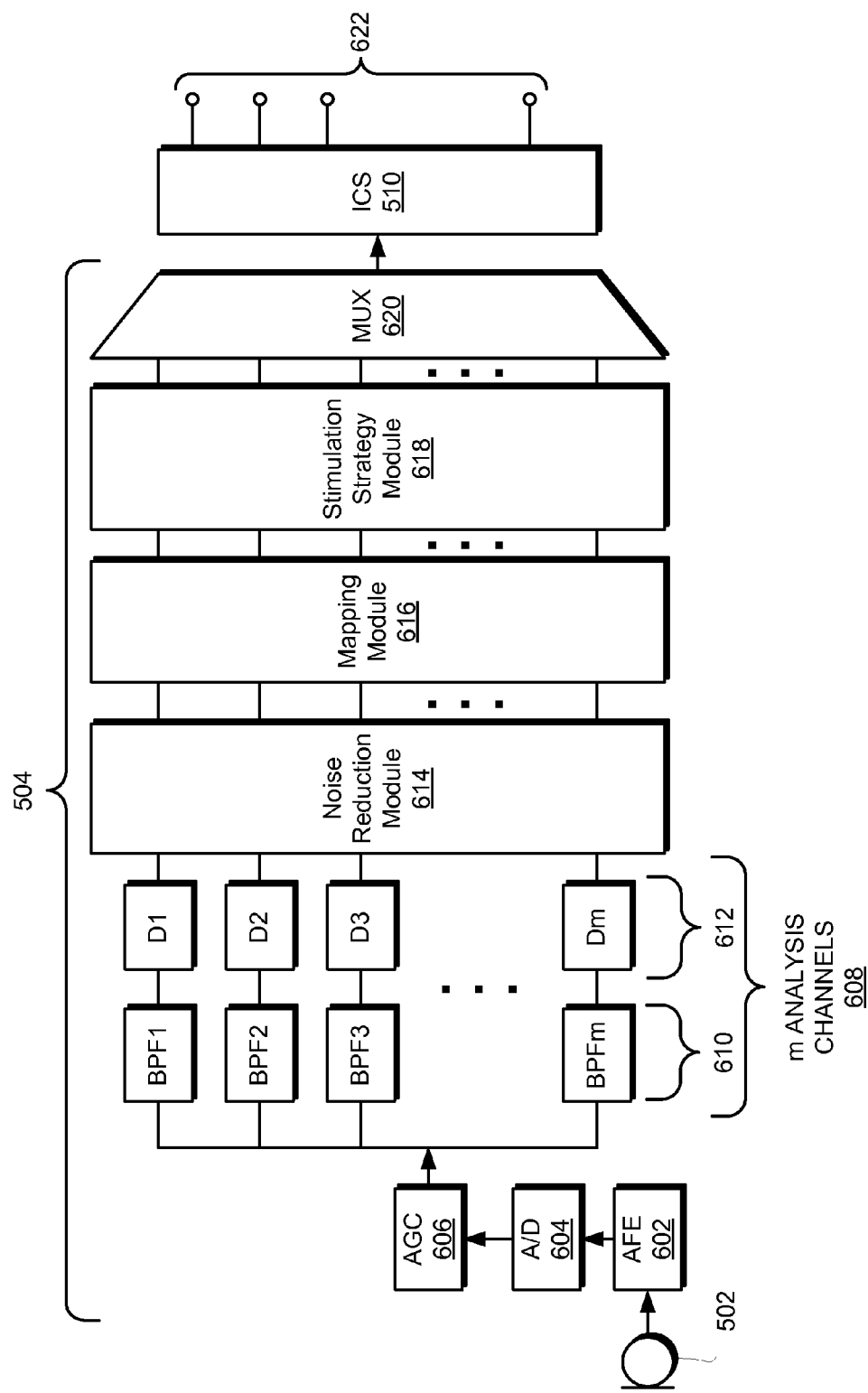
FIG. 6 illustrates components of an exemplary sound processor coupled to an implantable cochlear stimulator according to principles described herein.

FIG. 6 illustrates components of an exemplary sound processor 504 coupled to an implantable cochlear stimulator 510. The components shown in FIG. 6 may be configured to perform one or more of the processes associated with one or more of the facilities 302-316 associated with sound processing subsystem 102 and are merely representative of the many different components that may be included within sound processor 504.

As shown in FIG. 6, microphone 502 senses an audio signal, such as speech or music, and converts the audio signal into one or more electrical signals. These signals are then amplified in audio front-end ("AFE") circuitry 602. The amplified audio signal is then converted to a digital signal by an analog-to-digital ("A/D") converter 604. The resulting digital signal is then subjected to automatic gain control using a suitable automatic gain control ("AGC") unit 606.

After appropriate automatic gain control, the digital signal is subjected to a plurality of filters 610 (e.g., a plurality of band-pass filters). Filters 610 are configured to divide the digital signal into m analysis channels 608 each containing a signal representative of a distinct frequency portion of the audio signal sensed by microphone 502. Additional or alternative components may be used to divide the signal into the analysis channels 608 as may serve a particular application. For example, as described previously, one or more components may be included within sound processor 504 that are configured to apply a Discrete Fourier Transform to the audio signal and then divide the resulting frequency bins into the analysis channels 608.

As shown in FIG. 6, the signals within each analysis channel 608 may be input into an energy detector 612. Each energy detector 612 may include any combination of circuitry configured to detect an amount of energy contained within each of the signals within the analysis channels 608. For example, each energy detector 612 may include a rectification circuit followed by an integrator circuit.

In some examples, energy detectors 612 may be used to identify one or more spectral peaks and/or other spectral components included within each signal contained within analysis channels 608. For example, energy detectors 612 may be configured to detect a maximum energy level, average energy level, and/or any other energy characteristic of the signals within analysis channels 608. The detected energy levels may be used to identify spectral peaks and/or other spectral components of an audio signal as described herein.

After energy detection, the signals within the m analysis channels 608 may be input into a noise reduction module 614. Noise reduction module 614 may perform one or more of the functions described in connection with noise reduction facility 308. For example, noise reduction module 614 may generate a noise reduction gain parameter for each of the signals within analysis channels 608 based on a signal-to-noise ratio of each respective signal and apply noise reduction to the signals in accordance with the determined noise reduction gain parameters.

Mapping module 616 may perform one or more of the functions described in connection with mapping facility 310. For example, mapping module 616 may map the signals in the analysis channels 608 to one or more stimulation channels after the signals have been subjected to noise reduction by noise reduction module 614. For example, signal levels of the noise reduced signals generated by noise reduction module 614 are mapped to amplitude values used to define the electrical stimulation pulses that are applied to the patient by implantable cochlear stimulator 510 via M stimulation channels 622. In some examples, groups of one or more electrodes 514 may make up the M stimulation channels 622.

Stimulation strategy module 618 may perform one or more of the functions described in connection with stimulation strategy facility 312. For example, stimulation strategy module 618 may generate one or more stimulation parameters by selecting a particular stimulation configuration in which implantable cochlear stimulator 510 operates to generate and apply electrical stimulation representative of various spectral components of an audio signal. For example, stimulation strategy module 618 may be configured to generate stimulation parameters that direct implantable cochlear stimulator 510 to use partial multipolar stimulation to generate and apply electrical stimulation representative of the one or more spectral peaks of an audio signal. Stimulation strategy module 618 may additionally be configured to generate stimulation parameters that direct implantable cochlear stimulator 510 to use monopolar stimulation to generate and apply electrical stimulation representative of the one or more other spectral components of the audio signal.

Multiplexer 620 may be configured to serialize the stimulation parameters generated by stimulation strategy module 618 so that they can be transmitted to implantable cochlear stimulator 510 via coil 508. The implantable cochlear stimulator 510 may then generate and apply electrical stimulation via one or more of the M stimulation channels 622 to one or more stimulation sites within the duct of the patient's cochlea in accordance with the one or more stimulation parameters.

Figure 7:
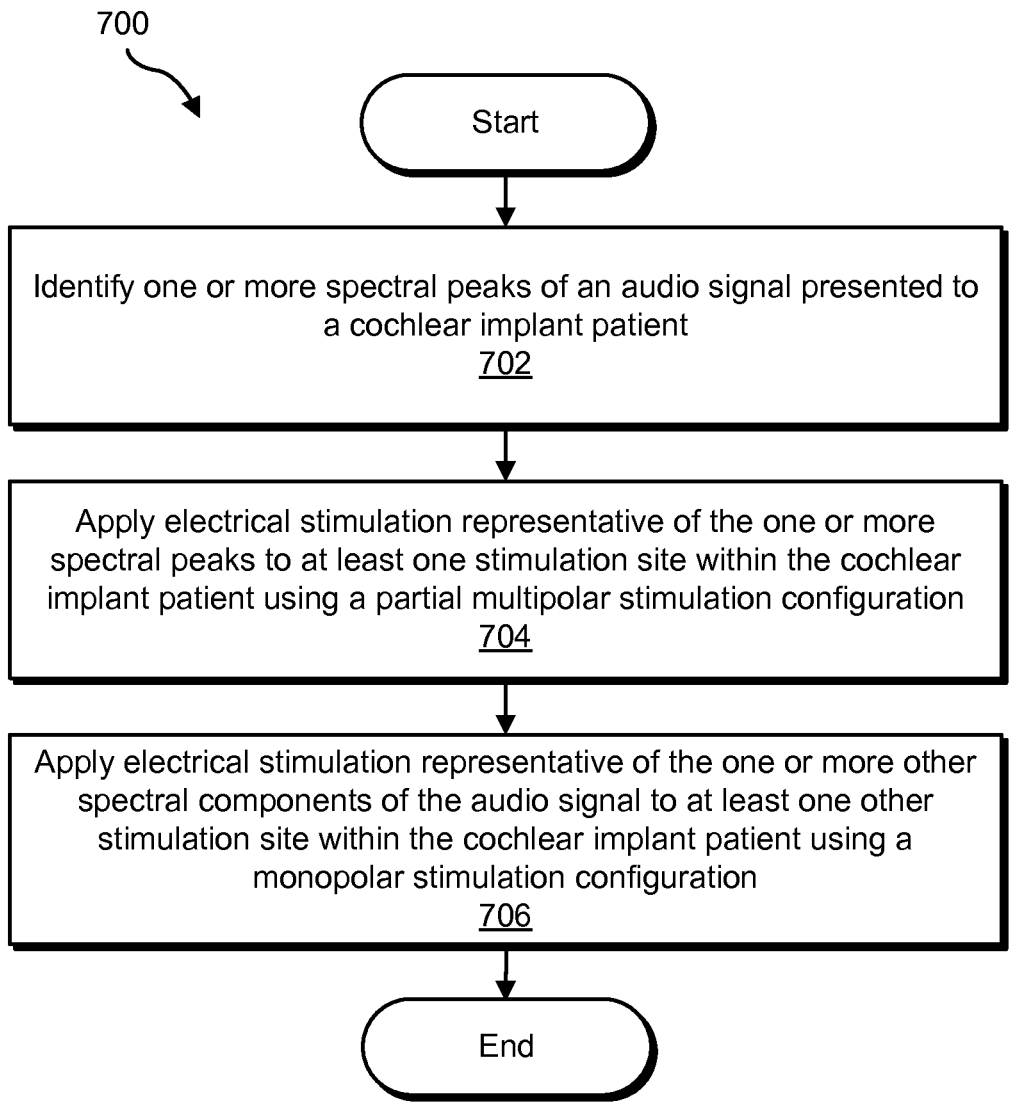
FIG. 7 illustrates an exemplary method of representing different spectral components of an audio signal presented to a cochlear implant patient according to principles described herein.

FIG. 7 illustrates an exemplary method 700 of representing different spectral components of an audio signal presented to a cochlear implant patient. While FIG. 7 illustrates exemplary steps according to one embodiment, other embodiments may omit, add to, reorder, and/or modify any of the steps shown in FIG. 7. It will be recognized that any of the systems, subsystems, facilities, and/or modules described herein may be configured to perform one or more of the steps shown in FIG. 7.

In step 702, one or more spectral peaks of an audio signal presented to a cochlear implant patient are identified. Step 702 may be performed by spectral analysis facility 306, for example, in any of the ways described herein.

In step 704, electrical stimulation representative of the one or more spectral peaks is applied to at least one stimulation site within the cochlear implant patient using a partial multipolar stimulation configuration. Exemplary partial multipolar stimulation configurations that may be used to apply electrical stimulation to at least one stimulation site within a cochlear implant patient will be described in more detail below.

In step 706, electrical stimulation representative of one or more other spectral components of the audio signal is applied at least one stimulation site within the cochlear implant patient using a monopolar stimulation configuration. An exemplary monopolar stimulation configuration that may be used to apply electrical stimulation to at least one stimulation site within a cochlear implant patient will be described in more detail below.

Figure 8:
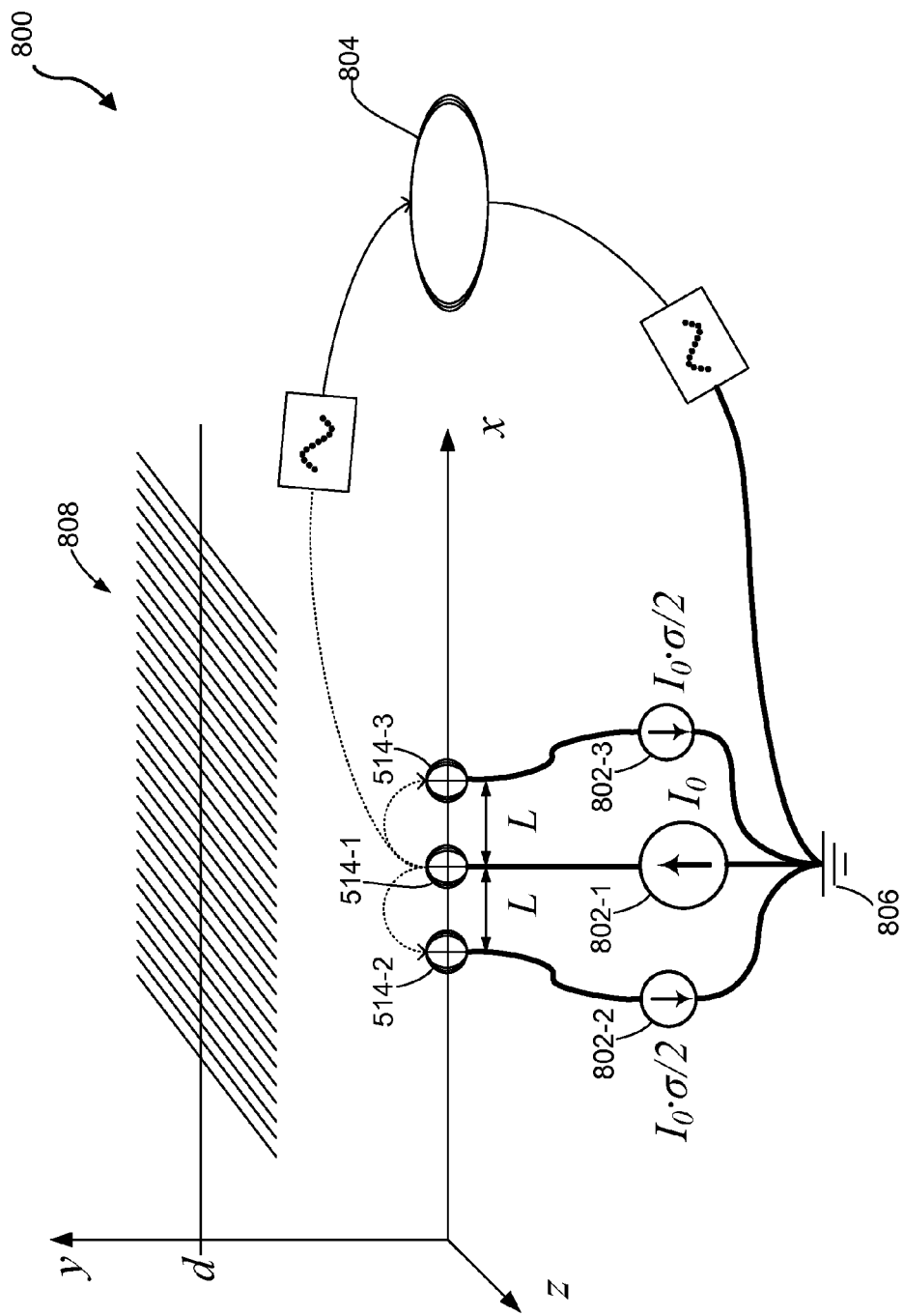
FIG. 8 shows an exemplary electrode arrangement that may be selectively configured to operate in one of a monopolar stimulation configuration, a full multipolar stimulation configuration, and a partial multipolar stimulation configuration according to principles described herein.

Exemplary stimulation configurations that may be used in connection with the systems and methods described herein will now be described. FIG. 8 shows an exemplary electrode arrangement 800 that may be selectively configured to operate in one of a monopolar stimulation configuration, a full multipolar stimulation configuration, and a partial multipolar stimulation configuration.

As shown in FIG. 8, electrode arrangement 800 may include a main intracochlear electrode 514-1 and plurality of compensating intracochlear electrodes (e.g., electrodes 514-2 and 514-3) surrounding main electrode 514-1. Electrodes 514-1 through 514-3 will be collectively referred to herein as "electrodes 514". An independent current source 802 (e.g., current sources 802-1 through 802-3) may correspond to each electrode 514. Current sources 802 may be included within implantable cochlear stimulator 510, for example, and may be configured to generate the stimulation current that is applied to each electrode 514.

In some examples, electrodes 514 are collinearly positioned a certain distance d away from a stimulation site 808 (e.g., the auditory nerve). For example, the electrodes 514 shown in FIG. 8 are collinearly located along a particular axis (e.g., the x-axis). Moreover, as shown in FIG. 8, the electrodes 514 may be separated one from another by a separation distance L. The separation distance L and the distance d may vary as may serve a particular application. It will also be recognized that electrodes 514 may be positioned in any alternative arrangement as may serve a particular application. For example, the electrodes 514 may be located within different planes.

Three intracochlear electrodes 514 are shown in FIG. 8 for illustrative purposes. The three intracochlear electrodes 514 may be configured to selectively operate in one of a monopolar stimulation configuration, a full tripolar stimulation configuration, and a partial tripolar stimulation configuration. It will be recognized that any other number of intracochlear electrodes 514 may be included within electrode configuration 800 in order to realize other types of full and/or partial multipolar stimulation. For example, two intracochlear electrodes 514 may be used to realize full and/or partial bipolar stimulation and/or four intracochlear electrodes 514 may be used to realize full and/or partial quadrapolar stimulation.

Electrode arrangement 800 may further include an extracochlear ground electrode 804 and a circuit ground 806. Extracochlear ground electrode 804 may be implemented using the case of implantable cochlear stimulator 510, disposed on a proximal portion of a lead that is inserted into the cochlea, and/or otherwise implemented in any suitable manner. Circuit ground 806 may include a ground trace, for example, disposed within implantable cochlear stimulator 510. As will be described in more detail below, a portion of the stimulation current applied to electrodes 514-1 through 514-3 may be returned to circuit ground 806 by way of extracochlear ground electrode 804 when electrodes 514 are configured to operate in a partial multipolar stimulation configuration.

Stimulation current may be selectively and simultaneously applied to one or more of electrodes 514-1 through 514-3 by one or more of current sources 802 in order to realize monopolar stimulation, full multipolar stimulation, and/or partial multipolar stimulation. To illustrate, FIG. 8 shows that a stimulation current $I_0$ may be applied to main electrode 514-1. The stimulation current $I_0$ may be generated by implantable cochlear stimulator 510, for example, in accordance with one or more stimulation parameters provided by sound processor 504 as may serve a particular application.

Current may also be applied to compensating electrodes 514-2 and 514-3 in order to narrow the excitation field caused by main electrode 514-1. The compensating current is opposite in phase as the stimulation current $I_0$ and may be represented by $I_0*\sigma/2$, wherein $\sigma$ represents a programmable multiplication factor or "focusing factor" ranging from 0 to 1. Hence, the total compensating current applied to compensating electrodes 514-2 and 514-3 may be varied from 0 to $I_0$. By so doing, stimulation current may be selectively applied to stimulation site 808 in a monopolar stimulation configuration, a full multipolar stimulation configuration, or a partial multipolar stimulation configuration.

To illustrate, a monopolar stimulation configuration may be realized by adjusting the focusing factor $\sigma$ to equal 0 in order to prevent current from being applied to compensating electrodes 514-2 and 514-3. In this manner, stimulation current is only applied to main electrode 514-1, thereby resulting in a monopolar stimulation configuration.

Alternatively, a full multipolar stimulation configuration may be realized by adjusting the focusing factor $\sigma$ to equal 1 in order to apply an equal amount of current via compensating electrodes 514-2 and 514-3 as is applied via the main electrode 514-1. In such a configuration, compensating current equal $I_0/2$ is applied to each of the compensating electrodes 514-2 and 514-3 shown in FIG. 8. Because the total amount of compensating current applied to compensating electrodes 514-2 and 514-3 is equal to the amount of current applied to main electrode 514-1, no current passes through extracochlear ground electrode 804 in full multipolar stimulation configuration. Full multipolar stimulation often results in undesirable side lobes that cause can produce significant pitch distortion and adversely affect speech perception in cochlear implant patients. Partial multipolar stimulation, on the other hand, does not result in as big of side lobes as does full multipolar stimulation, and therefore is more desirable to use to represent spectral peaks in an audio signal.

A partial multipolar stimulation configuration may be realized by adjusting the focusing factor $\sigma$ to a value in between, but not including, 0 and 1 such that the total amount of current applied by compensating electrodes 514-2 and 514-3 is greater than 0 and less than $I_0$. In such a stimulation configuration, an amount of current equal to $(1-\sigma)*I_0$ returns to circuit ground 806 by way of extracochlear ground electrode 804. For example, if focusing factor $\sigma$ is equal to 0.5, half of stimulation current $I_0$ flows through compensating electrodes 514-2 and 514-3 to circuit ground 806 and half of stimulation current $I_0$ flows through extracochlear ground electrode 804 to circuit ground 806.

Compensating electrodes 514-2 and 514-3 shown in FIG. 8 are both configured to apply an equal amount of compensating current (i.e., $I_0*\sigma/2$) for illustrative purposes only. It will be recognized that compensating electrodes 514-2 and 514-3 may alternatively be configured to apply different amounts of compensating current as may serve a particular application.

In some examples, the systems and methods described herein may be used in connection with a current steering stimulation strategy. As used herein, a "current steering stimulation strategy" is one in which weighted stimulation current is applied concurrently to two or more electrodes by an implantable cochlear stimulator in order to stimulate a stimulation site located in between areas associated with the two or more electrodes and thereby create a perception of a frequency in between the frequencies associated with the two or more electrodes, compensate for one or more disabled electrodes, and/or generate a target pitch that is outside a range of pitches associated with an array of electrodes. Current steering may be used for any other reason as may serve a particular application and will be described in more detail below.

Figure 9:
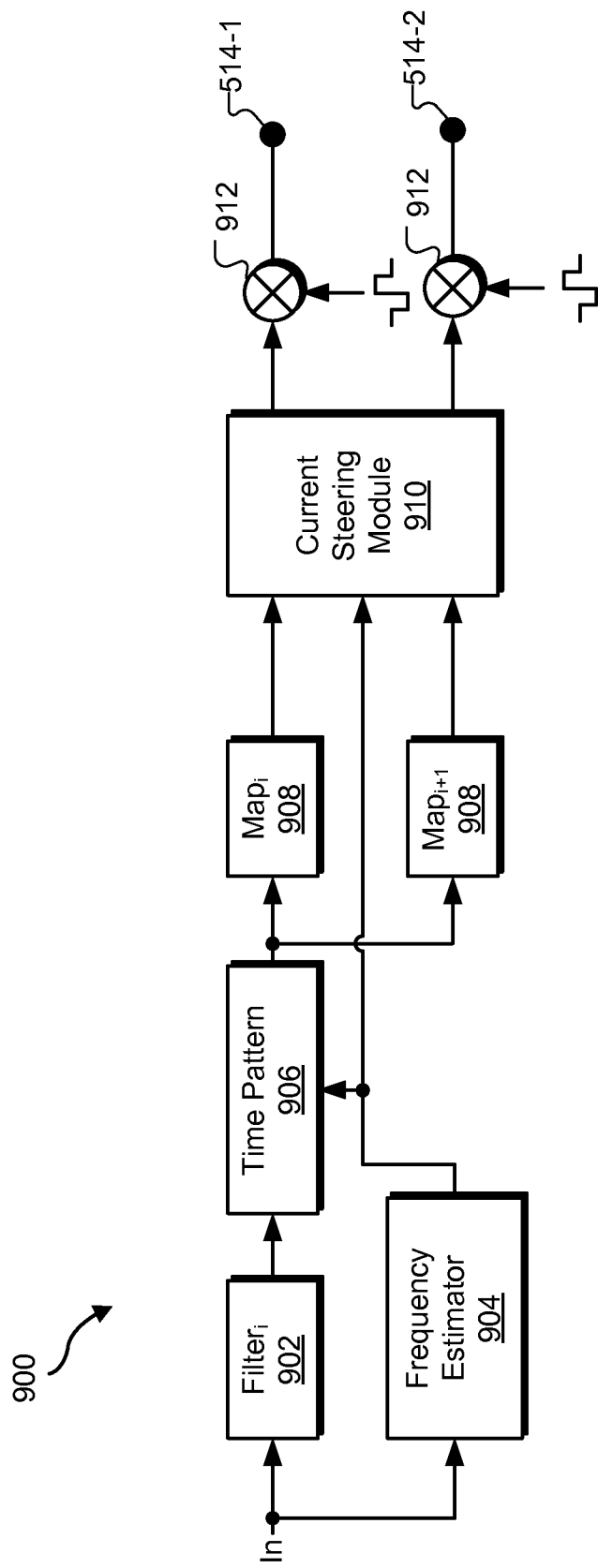
FIG. 9 illustrates an exemplary implementation of a current steering strategy according to principles described herein.

FIG. 9 illustrates an exemplary implementation 900 of a current steering strategy. The components and functions illustrated in FIG. 9 may be implemented by any of the subsystems, facilities, and/or modules described herein. For examples, one or more components of sound processor 504 may be configured to perform any of the functions described in connection with FIG. 9.

As shown in FIG. 9, current steering may be applied to two or more electrodes 514 (e.g., electrodes 514-1 and 514-2). Two electrodes 514 are shown in FIG. 9 for illustrative purposes only. It will be recognized that current steering may alternatively be applied to three or more electrodes as may serve a particular application. Electrodes 514-1 and 514-2 may be adjacent one to another (i.e., no other electrode 514 is physically disposed in between them on lead 512). Alternatively, electrodes 514-1 and 514-2 may be non-adjacent (i.e., one or more electrodes 514 are physically disposed in between them on lead 512).

As shown in FIG. 9, an input signal may be filtered by at least one filter 902 configured to generate a frequency domain signal representative of a distinct frequency portion of the audio signal. The input signal is also input into a frequency estimator 904 configured to estimate the peak frequency thereof. A time pattern block 906 is configured to build construct the temporal structure of a pulse train representing the signal output by the at least one filter 902. Mapping modules 908 are configured to map the amplitude of the signal output by the time pattern block 906 to corresponding current levels in accordance with a suitable mapping function.

The output of each mapping module 908 is input into a current steering module 910. The current steering module 910 is also configured to receive the output of the frequency estimator 904. In some examples, the current steering module 910 is configured to determine appropriate weighting factors for current to be applied to electrodes 514-1 and 514-2. This determination may be based at least in part on the peak frequency estimate and the output of each of the mapping modules 908. The weighting factors may be applied to the current using multiplication blocks 912. In this manner, stimulation current may be delivered to a stimulation site located in between areas associated with electrodes 514-1 and 514-2.

Figure 10:
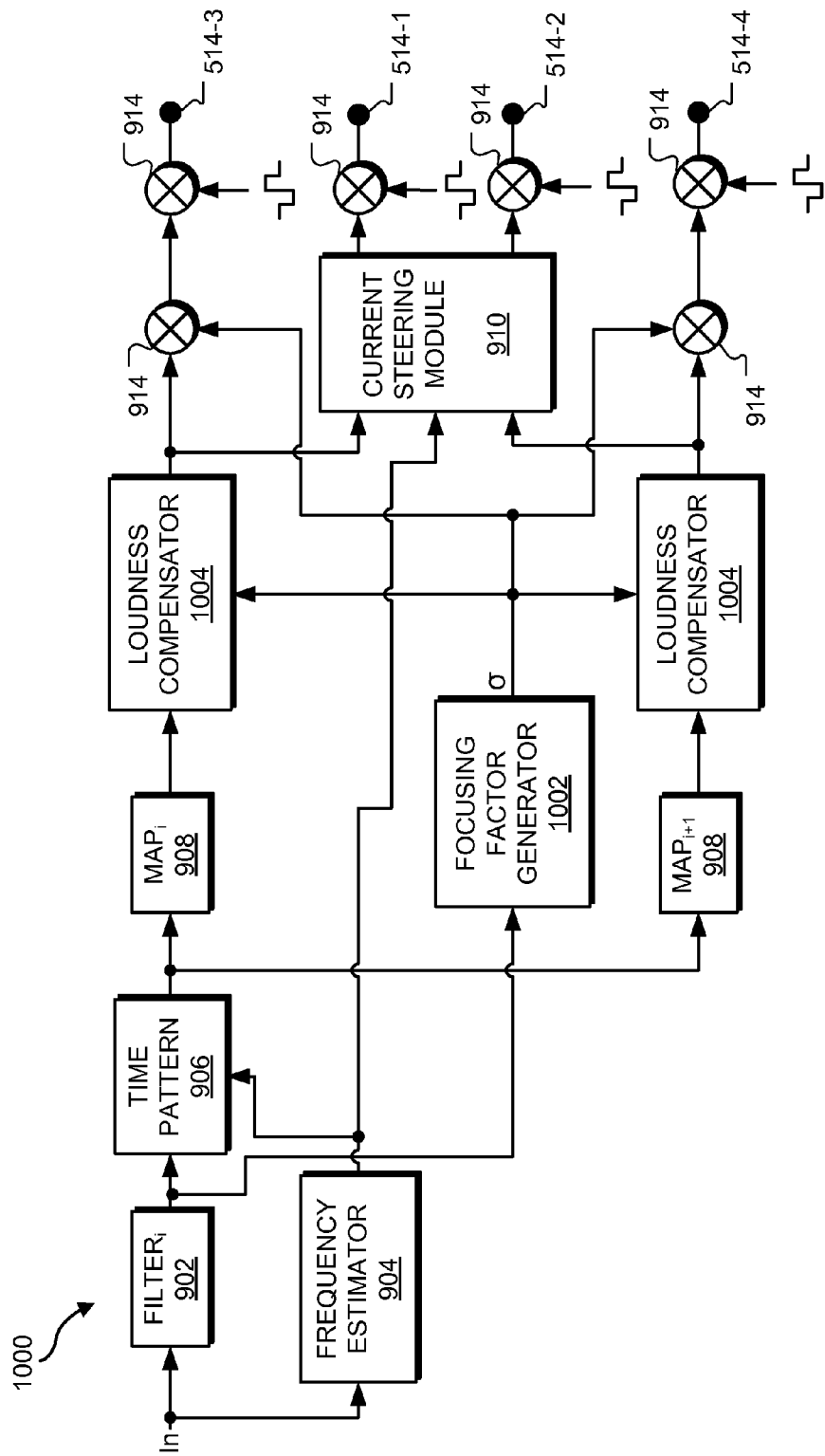
FIG. 10 illustrates another exemplary implementation of a current steering strategy according to principles described herein.

The excitation field produced by the current steering electrodes 514-1 and 514-2 may be narrowed by applying compensating current simultaneously via one or more additional electrodes. FIG. 10 illustrates another exemplary implementation 1000 of a current steering strategy that may be used to dynamically focus one or more excitation fields produced by current steering electrodes (e.g., electrodes 514-1 and 514-2). The components and functions illustrated in FIG. 10 may be implemented by any of the subsystems, facilities, and/or modules described herein. For examples, one or more components of sound processor 504 may be configured to perform any of the functions described in connection with FIG. 10.

Implementation 1000 includes many of the same components as the implementation described in connection with FIG. 9. In addition, functional block diagram 1000 includes a focusing factor generator 1002 configured to generate focusing factor $\sigma$ based on the amplitude of the signal output by filter 902. The focusing factor $\sigma$ is used to generate scaled versions of the current steering current. This scaled current is delivered via one or more additional electrodes (e.g., electrodes 514-3 and 514-4) to effectively narrow the excitation field produced by electrodes 514-1 and 514-2.

As shown in FIG. 10, loudness compensators 1004 may also be included within the implementation 1000 of FIG. 10. Loudness compensators 1004 are configured to adjust the amplitudes of the currents applied via electrodes 514-1 and 514-2 to compensate for loudness changes that may be caused by current delivered via the compensating electrodes 514-3 and 514-4.

While exemplary implementations 900 and 1000 of a current steering stimulation strategy have been described herein, it will be recognized that other implementations of a current steering stimulation strategy may additionally or alternatively used as may serve a particular application.

As mentioned, partial multipolar stimulation may be used to represent one or more formants included within an audio signal that comprises speech (i.e., a speech signal). A formant represents a resonance of the human vocal tract and is associated with the utterance of a vowel sound. There are often a plurality of formants that are associated with a particular vowel sound (e.g., formants $f_1$, $f_2$, and $f_3$, in descending order of amplitude). By representing one or more of the formants (e.g., at least the highest amplitude formant) corresponding to a particular vowel sound with partial multipolar stimulation instead of monopolar stimulation, the one or more formants may be represented more precisely thereby reducing spectral smearing and improving recognition of the vowel sound by the cochlear implant patient.

Figure 11:
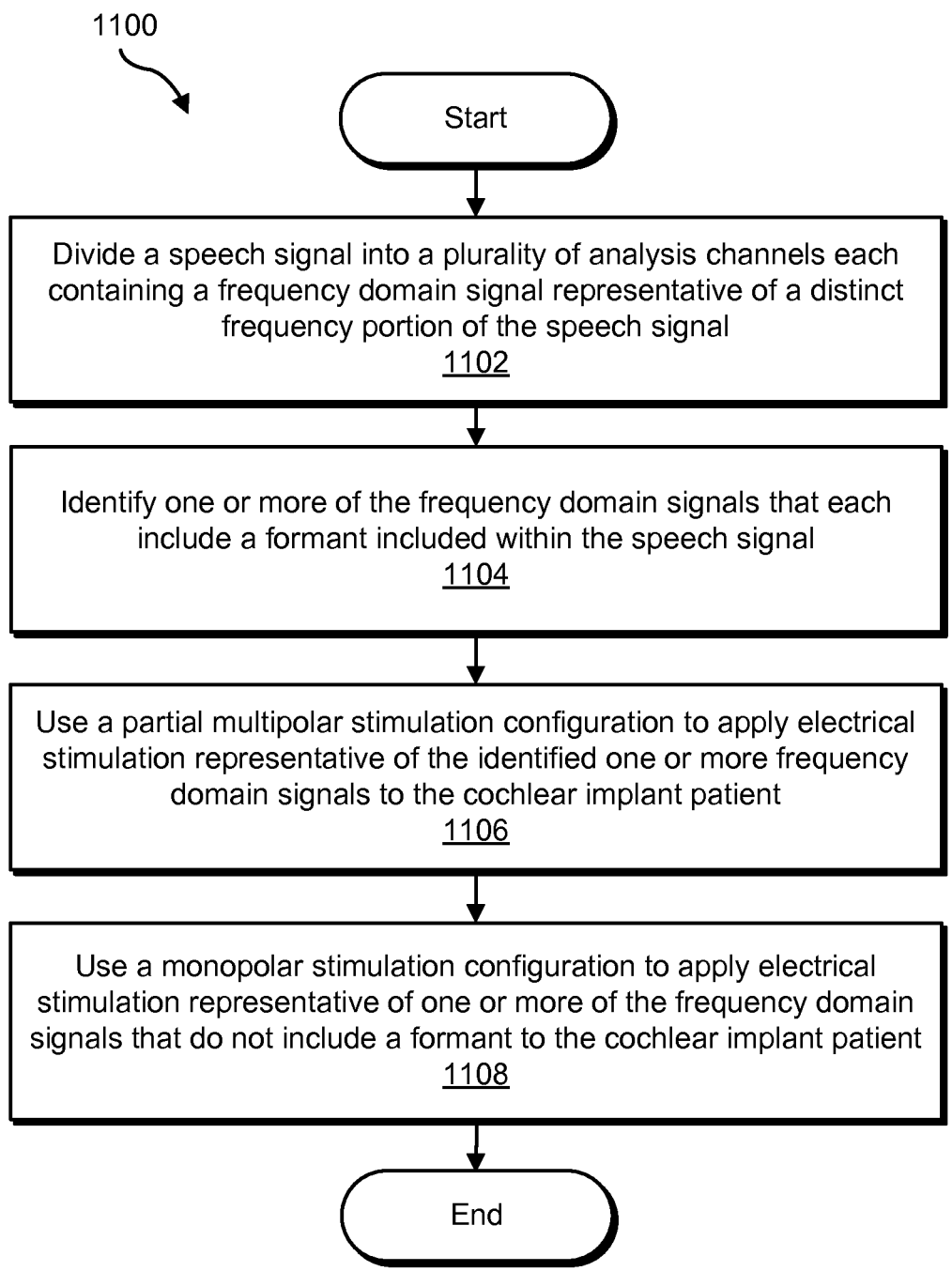
FIG. 11 illustrates an exemplary method of representing formants included within an audio signal presented to a cochlear implant patient according to principles described herein.

FIG. 11 illustrates an exemplary method 1100 of representing formants included within an audio signal presented to a cochlear implant patient. While FIG. 11 illustrates exemplary steps according to one embodiment, other embodiments may omit, add to, reorder, and/or modify any of the steps shown in FIG. 11. It will be recognized that any of the systems, subsystems, facilities, and/or modules described herein may be configured to perform one or more of the steps shown in FIG. 11.

In step 1102, a speech signal is divided into a plurality of analysis channels each containing a frequency domain signal representative of a distinct frequency portion of the speech signal. The speech signal may be divided into the plurality of analysis channels in any of the ways described herein.

In step 1104, one or more of the frequency domain signals that each include a formant included within the speech signal may be identified. The frequency domain signals that include formants may be identified in any of the ways described herein. For example, a maximum energy level of each of the frequency domain signals may be detected.

In step 1106, a partial multipolar stimulation configuration is used to apply electrical stimulation representative of the identified one or more frequency domain signals to the cochlear implant patient. The partial multipolar stimulation configuration may include any of the partial multipolar stimulation configurations described herein.

In step 1108, a monopolar stimulation configuration is used to apply electrical stimulation representative of one or more of the frequency domain signals that do not include a formant to the cochlear implant patient. The electrical stimulation may be applied to the cochlear implant patient in any of the ways described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A method comprising:
   dividing an audio signal presented to a cochlear implant patient into a plurality of analysis channels each containing a frequency domain signal representative of a distinct frequency portion of the audio signal;
   detecting a maximum energy level of each of the frequency domain signals;
   identifying, based on the detected maximum energy levels of each of the frequency domain signals, one or more spectral peaks and one or more other spectral components of the audio signal;
   selectively applying electrical stimulation representative of the one or more spectral peaks to at least one stimulation site within the cochlear implant patient using a partial multipolar stimulation configuration; and
   selectively applying electrical stimulation representative of the one or more other spectral components of the audio signal to at least one other stimulation site within the cochlear implant patient using a monopolar stimulation configuration;
   wherein the selectively applying of the electrical stimulation representative of the one or more spectral peaks using the partial multipolar stimulation configuration comprises concurrently
       applying a main current to a main electrode, and
       applying compensating current to one or more compensating electrodes,
       wherein the compensating current is opposite in polarity compared to the main current and less than the main current, and
       wherein a remaining amount of current equal to a difference between the main current and the compensating current flows to an extracochlear ground electrode.

2. The method of claim 1, wherein the identifying of the one or more spectral peaks comprises:
   designating a predetermined number of the detected maximum energy levels as corresponding to one of the one or more spectral peaks based on the detected maximum energy levels.

3. The method of claim 1, wherein the identifying of the one or more spectral peaks comprises:
   designating the detected maximum energy levels that are greater than a predetermined threshold value as corresponding to the one or more spectral peaks.

4. The method of claim 1, further comprising:
   generating one or more stimulation parameters based on the identified spectral peaks and the one or more other spectral components of the audio signal; and
   generating the electrical stimulation representative of the one or more spectral peaks and the electrical stimulation representative of the one or more other spectral components of the audio signal in accordance with the one or more stimulation parameters.

5. The method of claim 1, wherein the one or more spectral peaks comprise one or more formants within the audio signal.

6. The method of claim 1, wherein the one or more other spectral components of the audio signal comprise at least one spectral valley.

7. The method of claim 1, wherein the audio signal comprises speech.

8. The method of claim 1, wherein the partial multipolar stimulation configuration comprises one of a partial bipolar stimulation configuration and a partial tripolar stimulation configuration.

9. The method of claim 1, wherein the one or more compensating electrodes comprises two compensating electrodes adjacent to the main electrode.

\* \* \* \* \*